United States Patent

Seyler et al.

(10) Patent No.: US 8,383,227 B2
(45) Date of Patent: Feb. 26, 2013

(54) TRANSFER LAYER FOR ABSORBENT ARTICLE

(75) Inventors: Rickey J. Seyler, Chesterfield, VA (US); William C. Ancarrow, III, Ruther Glen, VA (US)

(73) Assignee: Tredegar Film Products Corporation, Richmond, VA (US)

(*) Notice: Subject to any disclaimer, the term of this patent is extended or adjusted under 35 U.S.C. 154(b) by 451 days.

(21) Appl. No.: 12/695,695

(22) Filed: Jan. 28, 2010

(65) Prior Publication Data

US 2011/0183109 A1 Jul. 28, 2011

(51) Int. Cl.
| B32B 3/24 | (2006.01) |
| B32B 3/30 | (2006.01) |
| A61F 13/15 | (2006.01) |
| A61F 13/539 | (2006.01) |
| A61F 13/511 | (2006.01) |
| A61F 13/514 | (2006.01) |

(52) U.S. Cl. ........ 428/132; 428/119; 428/120; 428/131; 428/137; 428/220; 604/378; 604/385.101

(58) Field of Classification Search .................. 428/132; 604/385.101

See application file for complete search history.

(56) References Cited

U.S. PATENT DOCUMENTS

| 3,945,386 A | 3/1976 | Anczurowski | |
|---|---|---|---|
| 3,967,623 A | 7/1976 | Butterworth | |
| 4,323,069 A | 4/1982 | Ahr | |
| 4,324,247 A | 4/1982 | Aziz | |
| 4,726,976 A | 2/1988 | Karami | |
| 5,078,710 A * | 1/1992 | Suda et al. | 604/383 |
| 5,171,238 A | 12/1992 | Kajander | |
| 5,342,334 A | 8/1994 | Thompson | |
| 5,352,217 A | 10/1994 | Curro | |
| 5,368,909 A | 11/1994 | Langdon | |
| 5,439,458 A | 8/1995 | Noel | |
| 5,509,915 A | 4/1996 | Hanson | |
| 5,522,811 A * | 6/1996 | Igaue et al. | 604/378 |
| 5,603,707 A | 2/1997 | Trombetta | |
| 5,614,283 A | 3/1997 | Potnis | |
| 5,635,275 A * | 6/1997 | Biagioli et al. | 428/132 |
| 5,643,240 A | 7/1997 | Jackson | |
| 5,846,230 A | 12/1998 | Osborn, III | |
| 5,998,696 A * | 12/1999 | Schone | 604/378 |
| 6,022,607 A * | 2/2000 | James et al. | 428/131 |
| 6,232,521 B1* | 5/2001 | Bewick-Sonntag et al. | 604/378 |
| 6,503,598 B1* | 1/2003 | Goda et al. | 428/137 |

(Continued)

FOREIGN PATENT DOCUMENTS

| EP | 0788874 A1 | 8/1997 |
| EP | 1621169 A2 | 1/2006 |

*Primary Examiner* — David Sample
*Assistant Examiner* — Jeff Vonch
(74) *Attorney, Agent, or Firm* — Condo Roccia LLP

(57) ABSTRACT

A composite particularly suited for use as a transfer layer in an absorbent article has a first layer comprising a formed film having a plurality of capillary-sized apertured protuberances and a plurality of two-dimensional drains, and a second layer in intimate contact with an apertured end of said capillary-sized protuberances and spaced from the first layer in a z-direction, the second layer is either a three-dimensional apertured formed film or a nonwoven web. In embodiments where the second layer is a three-dimensional formed film, the film contains a plurality of capillary sized protuberances that are of smaller diameter compared to the protuberances in the first layer and optionally also contains a plurality of drains, which can be either two-dimensional or three-dimensional, or combinations thereof.

17 Claims, 5 Drawing Sheets

U.S. PATENT DOCUMENTS

| | | | |
|---|---|---|---|
| 2002/0062113 A1* | 5/2002 | Thomas et al. | 604/378 |
| 2002/0082575 A1 | 6/2002 | Dan et al. | |
| 2003/0097101 A1 | 5/2003 | Schmidt et al. | |
| 2004/0002688 A1* | 1/2004 | Thomas et al. | 604/383 |
| 2004/0043189 A1 | 3/2004 | Huang | |
| 2004/0087927 A1* | 5/2004 | Suzuki | 604/378 |
| 2004/0161586 A1* | 8/2004 | Cree et al. | 428/131 |
| 2005/0256475 A1* | 11/2005 | Komatsu et al. | 604/378 |
| 2005/0261649 A1* | 11/2005 | Cohen | 604/383 |
| 2005/0267429 A1* | 12/2005 | Cohen | 604/378 |
| 2008/0114317 A1* | 5/2008 | Seyler | 604/369 |
| 2009/0182295 A1* | 7/2009 | Seyler | 604/378 |
| 2009/0299316 A1* | 12/2009 | Seyler | 604/378 |
| 2010/0121298 A1* | 5/2010 | Seyler et al. | 604/378 |
| 2011/0184370 A1* | 7/2011 | Seyler et al. | 604/385.101 |

* cited by examiner

TRANSFER LAYER FOR ABSORBENT ARTICLE

BACKGROUND OF THE DISCLOSURE

The disclosure relates to composite webs for use as transfer layers in absorbent articles.

Absorbent articles are articles that are generally used once or a limited number of times for the temporary collection and immobilization of bodily fluids. Such articles include diapers, adult incontinent products, feminine hygiene products, bandages and similar articles. In general, these articles have a topsheet, which is positioned adjacent the skin of the user, a backsheet, which is opposite the topsheet and may, in use, be positioned adjacent to the clothes of the wearer, and an absorbent core positioned between the topsheet and the backsheet. In most instances, the topsheet is pervious to the bodily fluids and the backsheet is impervious to such fluids, thus protecting the clothing of the wearer from leaks. The absorbent core is designed to collect and hold the bodily fluids until the article can be disposed of and replaced with a fresh article.

A transfer layer, which is also known in the art as an acquisition distribution layer or "ADL", has been used in absorbent articles. Both nonwoven webs and three-dimensional formed films have found use as transfer layer in the past. A transfer layer is typically positioned between the topsheet and the absorbent core and generally improves the efficiency of the article to absorb and retain fluids. For example, transfer layers have been used to provide void volume, which serves as a temporary reservoir to collect and hold fluids until the fluids can be absorbed by the core. In addition, transfer layers have been employed to promote lateral flow of fluids in a direction generally parallel to the plane of the transfer layer, thereby permitting more of the core to be used to absorb fluids. See, for example, U.S. Pat. No. 4,324,247.

There is a continuing need for transfer layers that more effectively promote distribution of fluids over the absorbent core, provide more comfort for the wearer, reduce surface wetness in the topsheet, and reduce or eliminate rewet in general.

SUMMARY OF THE DISCLOSURE

In One embodiment, the disclosure provides a transfer layer web comprising a first layer and a second layer, wherein the first layer comprises a formed film having three-dimensional capillaries and two-dimensional drains and the second layer comprises a formed film having three-dimensional capillaries, wherein the capillaries in the second layer are smaller than the capillaries in the first layer.

In another embodiment, the disclosure provides a transfer layer web comprising a first layer and a second layer, wherein the first layer comprises a formed film having three-dimensional capillaries and two-dimensional drains and the second layer comprises a formed film having three-dimensional capillaries, and two-dimensional drains, wherein the capillaries in the second layer are smaller than the capillaries in the first layer.

In another embodiment, the disclosure provides a transfer layer web comprising a first layer and a second layer, wherein the first layer comprises a formed film having three-dimensional capillaries and two-dimensional drains and the second layer comprises a formed film having three-dimensional capillaries and three-dimensional drains, wherein the capillaries in the second layer are smaller than the capillaries in the first layer and wherein said three-dimensional drains do not extend farther in the z-direction than said three-dimensional capillaries.

In another embodiment, the disclosure provides a transfer layer web comprising a first layer and a second layer, wherein the first layer comprises a formed film having three-dimensional capillaries and two-dimensional drains and the second layer comprises a nonwoven web.

These and other embodiments will be apparent from a reading of the detailed description, with reference to the drawings, and the appended claims.

DETAILED DESCRIPTION OF THE EMBODIMENTS

Figure 1:
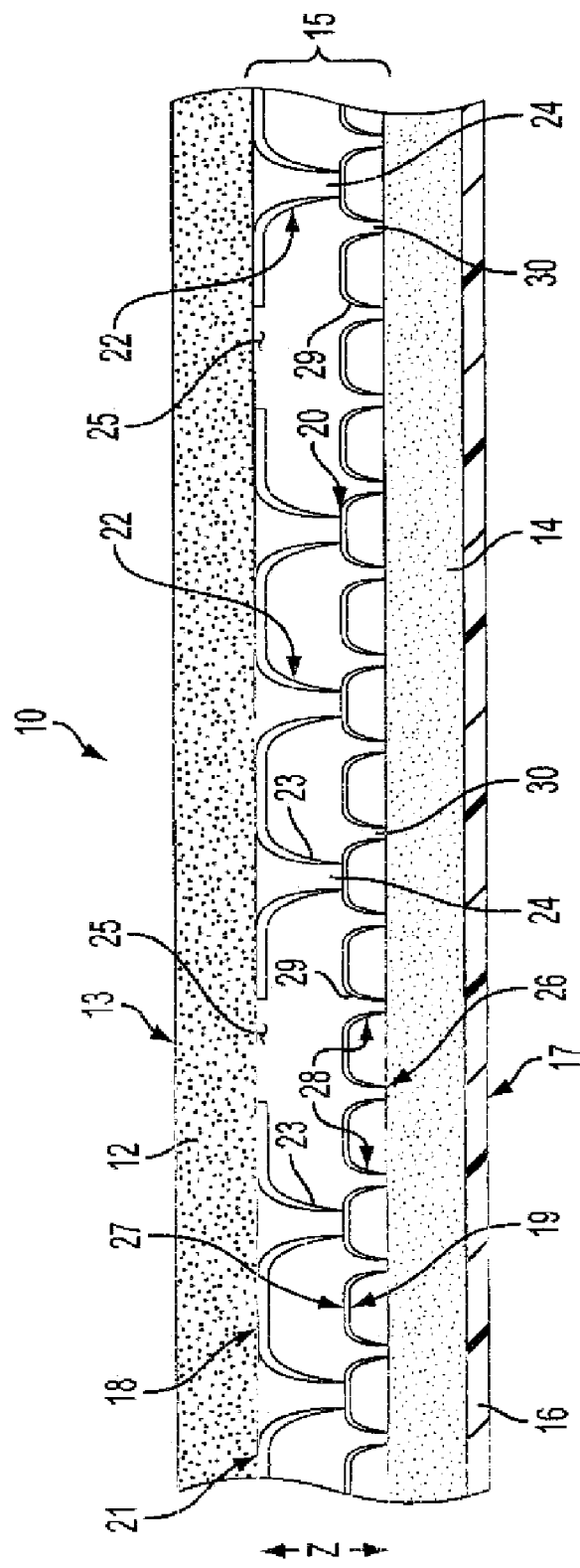
FIG. 1 is a cross-sectional view of an absorbent article having a transfer layer web in accordance with an embodiment of the disclosure.

Absorbent articles generally comprise a topsheet, an absorbent core, and a backsheet. The topsheet is on the body facing side of the absorbent article and typically comprises a liquid pervious material that allows liquid from an insult to transfer from the body-facing surface of the absorbent article to the absorbent core. The term "insult" generally refers to an amount of a liquid or the act of adding a liquid on a topsheet of an absorbent article. An insult may occur during product use and during finished product testing. Consequently, "multiple insults" occur when the same absorbent article is insulted more than once.

The topsheet is typically in close proximity or even direct contact with the wearer's skin during use and is typically made of a soft material such as a nonwoven material, an apertured film, or a combination of these materials made into a unitary composite. The topsheet is typically designed to retain a comfortable, dry feel to the wearer even after an insult.

The backsheet is positioned on the garment facing side or outside surface of the absorbent article. A backsheet may be a liquid impervious film that does not allow liquid to transfer from within the absorbent article to the exterior surface of the absorbent article or to the garment of the wearer. A breathable backsheet is impervious to liquid, yet allows water vapor to pass out of the absorbent article. This lowers the humidity felt by the wearer and thereby increases the comfort to the wearer.

The absorbent core absorbs the insult and retains the liquid while the absorbent article is in use. The absorbent core should adequately absorb an insult or multiple insults and substantially retain the insult until the absorbent article is removed and discarded. The storage capacity of the absorbent core and the efficiency of distribution of an insult across the absorbent core determine the amount of liquid that may be held in the absorbent article. The absorbent material in an absorbent core may comprise any liquid absorbent material such as, but not limited to cellulose materials including fibers, cellular sponge or foam materials, super absorbent materials, such as superabsorbent polymers, hydrocolloidal materials, gel materials and combinations thereof. It is within the contemplated scope of the present disclosure that one or more of these types of absorbent materials are useful in specific embodiments. In particular, in certain embodiments, the absorbent material may comprise a mixture of absorbent granular materials and finely chopped cellulose fibers.

Particularly useful absorbent materials are high absorbency gel-type materials which are generally capable of absorbing about 10 to about 50 times their weight in fluid. As is generally known in the art, the rate at which the core absorbs liquids is inversely proportional to the ability of the core to hold the liquids absorbed. Thus, the superabsorbent materials used in cores are very good at holding liquids, but are relatively slow at liquid uptake. The delay in liquid uptake results in more unabsorbed or "free" fluid in the article, which has the potential to increase back wetting and thus increase rewet. Because the superabsorbent materials have other benefits, such as reduced bulk of the core, the slower uptake is generally outweighed by the other advantages.

In accordance with the embodiments, the transfer layers are located between the topsheet and the absorbent core or between the backsheet and the absorbent core. Most preferably, the transfer layers are located between the topsheet and the core.

Transfer layers may function to control rewet, a phenomenon whereby unabsorbed or "free" fluid within the article is present on or within the user-contacting surface of the article. Rewet is comprised of a surface wetness component and a back wetting component. Surface wetness refers to liquids that remain on the surface of the topsheet or within the porosity of the topsheet after an insult. Back wetting refers to fluids that have once passed through the topsheet but transfer back to the topsheet surface. Back wetting is generally more pronounced when the article is under load or compression, whereby fluids are forced back through the topsheet. The compression can occur, for example, when an infant urinates in the diaper and then sits. Liquids present at or within the surface of the topsheet, by whatever mechanism, create an unpleasant, damp feeling to the user of the article. Thus, minimizing or eliminating rewet is important for consumer acceptance. Transfer layers can control rewet by providing a physical restriction to back wetting. In particular, a film material acts as a physical barrier because the film itself is liquid impermeable and the apertures are generally shaped to restrict the flow of liquids away from the absorbent core. Nonwoven transfer layers, however, provide a temporary reservoir and collect fluids before they reach the topsheet surface. In certain situations, transfer layers can also reduce surface wetness on the topsheet by facilitating transfer of stationary fluids that would otherwise tend to remain on the topsheet.

In standard industry tests, such as EDANA ERT 151.2-99 or EDANA ERT 151.3-02, rewet is measured by subjecting the article to a measured insult of fluid, waiting 0.10 minutes, and then applying blotter paper and a weight to the topsheet and measuring the amount of liquid acquired by the blotter paper. The reason for the 10 minute delay is to allow the absorbent core time to acquire the liquid. As a practical matter, however, the user of the article does not want the wet sensation to last for 10 minutes as it can be a very unpleasant feeling. Thus, from a consumer perspective, near instantaneous dryness following an insult is required.

An insult may be considered to include a combination of both dynamic and stationary fluid. The dynamic fluid flows through the topsheet and transfer layer at the time of insult while the stationary fluid may be retained within a porosity of the topsheet and/or transfer layer. To remove the stationary fluid, a transfer layer must be capable of sustaining z-direction wicking or capillary action. When the transfer layer is a three-dimensional formed film, z-direction wicking or capillary action is accomplished by providing at least a portion of the apertures that are sufficiently small in diameter to achieve capillarity or capillary action.

As mentioned, both films and nonwoven fibrous webs have been used as both topsheets and transfer layers. Nonwoven webs have internal void space between the fibers that can attract and hold liquids. Thus, nonwoven webs provide a temporary or "buffer" reservoir for fluids. When an insult occurs, fluids accumulate in the pore spaces of a nonwoven, whether it is used as a topsheet or a transfer layer, until the fluids have an opportunity to drain out and/or be absorbed by the core. The buffer function of the nonwoven works in both directions. Specifically, when an insult occurs, the nonwoven acts as a buffer to hold fluids until they can drain out and be absorbed by the core. Once the fluids have drained out, the nonwoven can act as a buffer to accumulate fluids before they reach the topsheet surface. The amount of fluids that drain out, and the time to do so, as well as the butler capacity of the nonwoven are dependent upon the size of the pores between the fibers of the nonwoven web, the relative hydrophilicity/hydrophobicity of the nonwoven, the fiber density, and other factors. Immediately after an insult, the void capacity of the nonwoven is essentially lull and the core has not had sufficient time to absorb the insult. Thus, there is no capacity for the nonwoven to act as a buffer to fluids transferring back to the topsheet surface. The portion of the insult that passes through the nonwoven web but is not yet absorbed, as well as the portion that is temporarily retained within the pores of the web can contribute to rewet.

With a formed film, however, except for a small amount of fluid that might remain in the land areas between the apertures, the insult is nearly instantaneously passed through the film and stored in the void space on the underside of the film. If a load is applied at that time, the film acts as a physical barrier to rewet and it is only the fluids that find their way back through the apertures that contribute to rewet. Because the apertures in formed films are typically tapered to have a narrower opening on one side (i.e.; the "male" side) verses the opposite or "female" side, the films exhibit a preferential liquid flow towards the core and are practically liquid impervious in the opposite direction. As a result, formed films can provide near instantaneous dryness in an absorbent article whereas nonwoven webs do not. Indeed, testing has shown that films are superior to nonwoven webs in rewet performance, particularly when tested immediately after an insult. With the passage of time following an insult, the nonwoven has an opportunity to drain out and can again function as a buffer to fluid transfer from the core area to the topsheet surface. Thus, the difference in rewet performance when using films as opposed to nonwoven webs is less significant as time after insult increases.

Reported in Table 1 are the grams of liquid obtained using a standard rewet test procedure as a function of time after insult.

TABLE 1

| sample | Time (minutes after insult) | | | | | |
|---|---|---|---|---|---|---|
| | 0 | 2 | 4 | 6 | 8 | 10 |
| Size 4 diaper with nonwoven transfer layer (first insult) | 16.32 | 0.51 | 0.50 | 0.30 | 0.24 | 0.32 |
| Size 4 diaper with film transfer layer (first insult) | 1.37 | 0.29 | 0.34 | 0.32 | 0.22 | 0.21 |
| Size 4 diaper with nonwoven transfer layer (third insult) | 48.65 | 32.71 | 22.31 | 17.68 | 20.05 | 12.97 |
| Size 4 diaper with film transfer layer (third insult) | 24.59 | 14.25 | 9.17 | 5.43 | 5.34 | 4.77 |

Figure 5:
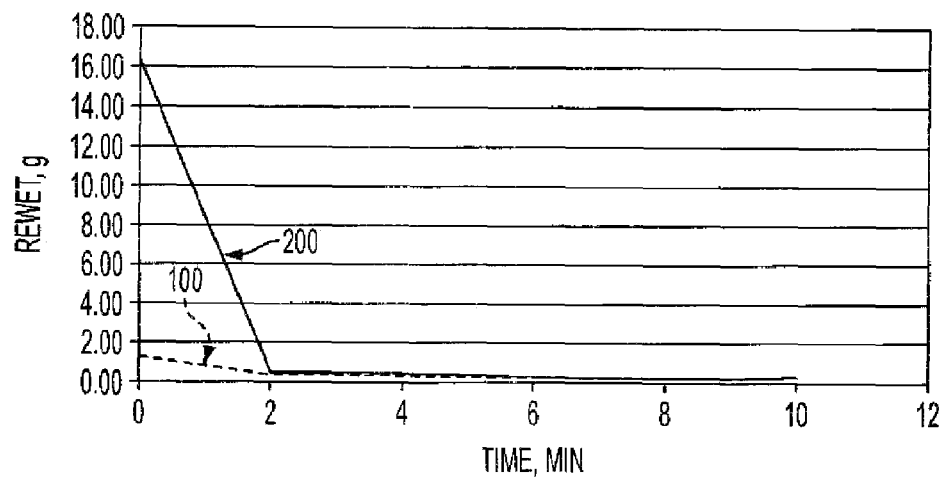
FIG. 5 is a graph of grams of liquid versus time.
Figure 6:
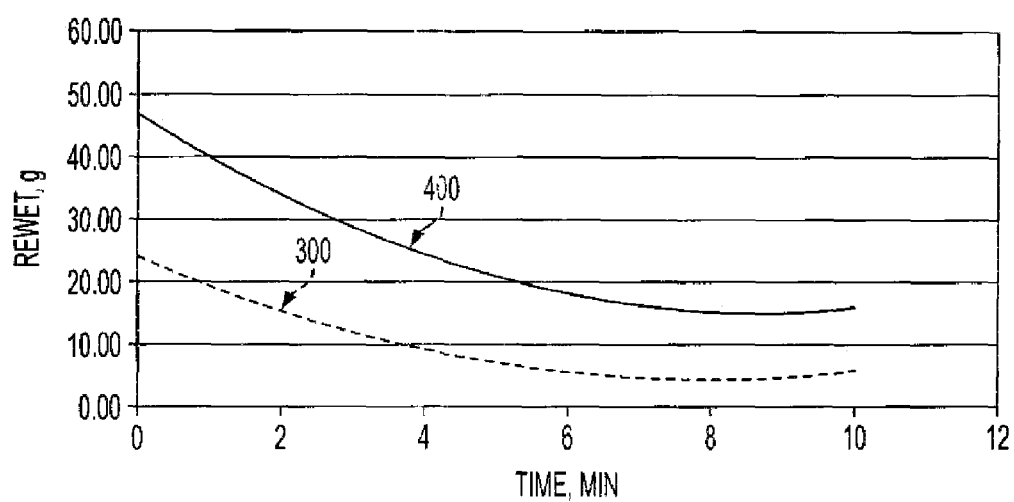
FIG. 6 is a graph of grams of liquid versus time

The data from Table 1 is plotted and illustrated in FIGS. 5 and 6 as graphs of grams of fluid versus time. More specifically, FIG. 5 depicts results obtained when measuring rewet after acquisition of a first insult. Curve 100 represents an article using a film and curve 200 represents an article using a nonwoven. As seen in FIG. 5, the use of a film results in significantly less rewet immediately after insult as compared to using a nonwoven. In time, the difference between films and nonwovens is negligible, but films clearly provide a more immediate sensation of dryness. These data indicate that immediately after a first insult, baby diapers using nonwoven transfer layers can produce 6-16 grams more liquid in the rewet test as compared to identical articles using formed films.

With reference to FIG. 6, illustrated therein is a curve of grains liquid versus time of a rewet test after a third insult. The data show that articles using formed films as transfer layers (curve 300) showed significantly less surface liquids as compared to articles using nonwovens as transfer layers (curve 400). The difference is similar to that seen in the conditions for FIG. 5; i.e. the articles using formed films had 6-26 grams less liquid versus articles using nonwoven webs.

Transfer layers in accordance with the embodiments are composites of a film with either another film or a nonwoven web. The film/film combination provides a dual barrier functionality as referenced above. The film/nonwoven embodiment provides a barrier/buffer functionality. If a nonwoven web is used, it is preferred that the transfer layer be oriented with the nonwoven web closest to the absorbent core. This orientation takes full advantage of the physical barrier function of a film transfer layer and the buffer capacity of a nonwoven transfer layer. In either embodiment, the rewet performance in absorbent articles is significantly improved.

As used herein, a "film" refers to a thin polymer sheet or web. A film may be produced, for example, by extruding a molten thermoplastic polymer in a cast or blown extrusion process and may be further processed between rollers and cooled to form the web. Films can be monolayer films or coextruded films, for example.

The term "polymer" includes homopolymers, copolymers, such as, for example, block, graft, random and alternating copolymers, terpolymers, etc., and blends and modifications thereof. Furthermore, unless otherwise specifically limited, the term "polymer" is meant to include all possible geometrical configurations of the material, such as isotactic, syndiotactic and atactic or random symmetries.

Nonwoven webs are fibrous webs comprised of polymeric fibers arranged in a random or non-repeating pattern. Nonwoven webs can generally be classified as continuous or staple fiber webs. Examples of continuous fiber webs include meltblown and spunbonded webs. Examples of webs having staple fibers include carded webs. The individual fibers are formed into a coherent web by any one or more of a variety of processes, such as thermal bonding (calendaring), hyrdoentangling, resin bonding, or other methods known in the art. The fibers used to make the webs may be a single component or a bi-component fiber as is known in the art.

Term "meltblown fibers" refers to fibers formed by extruding a molten thermoplastic material through a plurality of fine, usually circular, die capillaries as molten threads or filaments into a high velocity gas (e.g., air) stream that attenuates the filaments of molten thermoplastic material to reduce their diameter, which may be to a microfiber diameter. The term "microfibers" refers to small diameter fibers having an average diameter not greater than about 100 microns. Thereafter, the meltblown fibers are carried by the high velocity gas stream and are deposited on a collecting surface to form a web of randomly dispersed meltblown fibers.

The term "spunbonded fibers" refers to small diameter fibers that are formed by extruding a molten thermoplastic material as filaments from a plurality of fine, usually circular, capillaries of a spinneret with the diameter of the extruded filaments then being rapidly reduced as by, for example, eductive drawing or other well-known spunbonding mechanisms.

The transfer layers may be dimensionally described as having a machine direction, a cross direction, and a z-direction. The machine direction is defined by the direction in which the film passes through the manufacturing process. Typically, films are produced as long sheets or webs having a much greater length than width. In such a case, the machine direction is usually the length (also referred to as the x-direction) of the sheet. Perpendicular to the machine direction is the cross direction or transverse direction (also referred to as the y-direction or width) of the sheet. The thickness of the film (sometimes also referred in certain embodiments as loft or caliper of the film) is measured in the z-direction.

Three-dimensional formed films include a base plane forming the nominal thickness of the film, and include structures originating on the surface of the film and protruding outwardly in the z-direction. The dimensions of these structures provide the film with a z-direction dimension that is greater than the nominal thickness of the film. They also provide the film with a secondary plane defined by the surface structures and spaced from the base plane of the film in the z-direction. The three-dimensional features of the three-dimensional formed films may be produced in an embossing process, a hydroforming process, or a vacuum forming process, for example. All such processes are well known in the art.

A "multiplanar film" is a three-dimensional formed film that has additional surface structures that originate from both the base plane and any secondary plane(s) of the film. For example, a formed film having a multiplanar structure may comprise a plurality of plateaus that extending from the surface of the film, the plateaus defining at least one additional plane of the film above or below the base surface. In certain embodiments of the multiplanar three-dimensional formed film, protuberances may be formed on any or all of the available planes.

A three-dimensional apertured formed film is simply a formed film that has openings or apertures in the three-dimensional structures. The size, spacing and other properties of the apertured three-dimensional structures are based upon the particular apparatus used to create the three-dimensional apertured formed film. For example, in a vacuum forming process, a hydroforming process, and some mechanical processes, the size, shape and spacing of the apertures is determined by the forming structure that supports the film while the film is subjected to vacuum pressure, pressurized water streams, or mechanical perforation devices such as pins. See, for example U.S. Pat. No. 4,456,570 and U.S. Pat. No. 3,929,135.

For apertured formed films, the z-direction dimension of the three-dimensional structure is a function of the diameter of the three-dimensional structure, which, in turn, is a function of the diameter of the apertures in the forming structure or the diameter of the perforating pin. For example, smaller diameter structures typically have a smaller z-direction dimension as compared to larger diameter structures. Other factors also contribute to the z-direction height of the three-dimensional features such as film composition, basis weight of the film, temperature of the film while being apertured, as well as other process conditions and apparatus-related factors.

For example, three-dimensional formed films may comprise at least one polymer selected from polyolefins (e.g., C2-C10 olefins such as polyethylene, polypropylene, etc.); polyesters; plastomers; polyamides (e.g., nylon); polystyrenes; polyurethanes; vinyl polymers; acrylic and/or methacrylic polymers; elastomers (e.g., styrene block copolymer elastomers); polymers from natural renewable sources; biodegradable polymers; and mixtures or blends thereof. Preferably, the polymer is a thermoplastic polymer.

Additionally, any of a variety of additives may be added to the polymers and may provide certain desired characteristics, including, but not limited to roughness, reduction of antistatic charge build-up, abrasion resistance, printability, writeability, opacity, hydrophilicity, hydrophobicity, processability, UV stabilization, color, etc. Such additives are well known in the industry and include, for example, calcium carbonate (abrasion resistance), titanium dioxide (color and opacity), silicon dioxide (roughness), surfactants (hydrophilicity/hydrophobicity), process aids/plastomers (processability), etc.

The transfer layer webs comprise a laminate or composite structure. The terms "laminate" and "composite" are synonymous and refer to two or more sheet-like members or webs joined together in a surface-to-surface relationship to form a unitary web. The term "unitary web" refers to a layered web comprising two or more webs of material, including nonwoven webs that are sufficiently joined, such as by thermal bonding means, to be handled, processed, or otherwise utilized, as a single web.

Laminates may be formed by coextrusion, or any number of lamination processes, including thermal lamination, adhesive lamination, ultrasonic lamination, pressure lamination, extrusion coating, vacuum lamination and other lamination techniques known in the art, and combinations thereof.

Referring to the embodiment of FIG. 1, absorbent article 10 comprises a topsheet 12, a core 14, a backsheet 16 and a transfer layer 15 positioned between the core 14 and topsheet 12. The article 10 has a body facing surface 13 which, in use, would be placed adjacent to or otherwise in close proximity with the skin of the user. The article 10 also has a garment facing surface 17 which is opposite the body facing surface 13. The garment facing surface 17, in use, would be in proximity to the garment of the user or to the environment if the absorbent article is a bandage, wound dressing, surgical drape or the like.

Topsheet 12 comprises a fluid pervious material to allow fluids to enter the absorbent article 10. Topsheet 12 is generally an apertured film, such as an apertured formed film, a nonwoven web, or composites. In the embodiments illustrated, the topsheet 12 comprises a nonwoven web. Backsheet 16 is generally fluid impervious to prevent leakage of fluids from the absorbent article. Films, nonwoven webs and composites are typically used for the backsheet. In the embodiments shown, the backsheet 16 comprises a liquid impervious blown or cast film. The absorbent core 14 is between the topsheet 12 and the backsheet 16 and comprises materials that can absorb and retain fluids that pass through the topsheet until the article is discarded.

As seen in FIG. 1, the transfer layer 15 comprises a first layer 18 and a second layer 19. The first layer, in this and all other embodiments, comprises a three-dimensional apertured formed film with a male side 20 and a female side 21. The first layer 18 has a plurality of protuberances 22 comprising cone-shaped structures with side walls 23 that extend in a z-direction (indicated by arrow "Z" in FIG. 1) from the female side 21 of the film 18. The protuberances 22 terminate in an aperture 24 on the male side 20 of the film 18. The first layer 18 further includes drains 25.

Although both drains 25 and protuberances 22 provide for fluid management, they operate in different manners. Drains 25 are larger diameter compared to the diameter of protuberances 22. Thus, drains 25 are capable of handling large insults of fluid and provide little or no appreciable resistance to fluid flow through the first layer 18. In addition, drains 25 are two-dimensional in that they lack any z-direction dimension beyond the nominal thickness of the film.

By contrast, protuberances 22 are sized to provide fluid transport via capillary action and promote removal of a stationary portion of the insult retained on the topsheet surface or within the porosity of the topsheet by providing sustained z-direction wicking. The z-direction wicking improves rewet performance by reducing either the surface wetness component or the back wetting component, or both. This z-direction wicking is accomplished by providing the protuberances 22 with a diameter that is sufficiently small to achieve capillarity.

For sustained capillary action to occur, it is necessary to provide some mechanism to remove fluids from the exit side (i.e., at aperture 24) of the protuberance 22. One convenient mechanism in absorbent articles is to place the exit side of the capillary in intimate contact with another material. This has been difficult to execute in prior art transfer layers, however, particularly in transfer layers that also contain larger diameter protuberances. Specifically, the larger diameter protuberances, which are necessary to provide for rapid acquisition of the dynamic portion of an insult, would generally be of greater dimension in the z-direction than the smaller diameter capillaries. Accordingly, for the capillaries to make intimate contact with the core, the larger protuberances would need to be crushed, or compressed in the z-direction. This is, of course, contraindicated because it defeats the purpose of the larger protuberances. Accordingly, in prior art films, the capillaries would be suspended above the absorbent core in the void space and thus fail to provide for sustainable removal of liquid. Because drains 25 are two-dimensional, they do not interfere with the apertured end of protuberances 22 from making direct contact with second layer film 19, which provides the mechanism needed to maintained sustained capillary action in wicking fluids away from topsheet 12.

The drains 25 may be any desired size. For example, the drains 25 of certain embodiments may have an average cross sectional area greater than 0.2 mm$^2$ and an average hydraulic diameter between 0.55 mm and 1.2 mm. The protuberances 22, by contrast, have an average diameter between 50 microns and 400 microns as measured on the female side 21 of protuberances 22. The ratio of the hydraulic radius of the drains 25 to the protuberances 22 will generally exceed 3:1 and in most cases will be 4 or 5:1 or higher. Ratios of 10:1 or more are also common.

The second layer 19 of the composite transfer layer web 15 comprises a three-dimensional apertured formed film with a male side 26 and a female side 27. The second layer 19 has a plurality of protuberances 28 comprising cone-shaped structures with side walls 29 that extend in a z-direction from the female side 27 of the film 19. The protuberances 28 terminate in an aperture 30 on the male side 26 of the film 19. The diameter of the protuberances 28 in the second layer 19 is equal to or less than the diameter of the protuberances 22 in the first layer 18. In particularly, in preferred embodiments the apertures 28 are capillary sized and less than the diameters of protuberances 22, thus creating a capillary gradient that continues to 'pump' residual stationary fluid from the nonwoven topsheet 12. Furthermore, the apertures 30 must be in contact with the core (which acts as the mass removal mechanism) to sustain the z-direction wicking.

Figure 2:
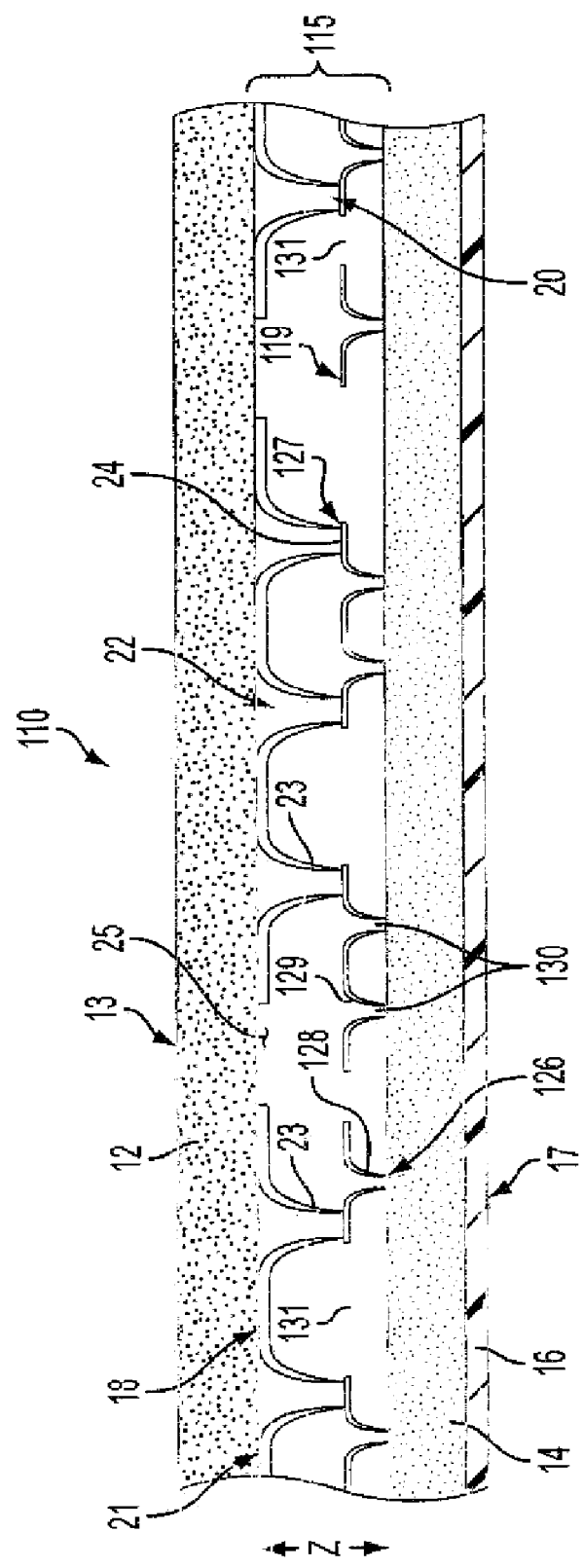
FIG. 2 is a cross-sectional view of an absorbent article having a transfer layer web in accordance with another embodiment of the disclosure.

With reference to the embodiment of FIG. 2, the topsheet 12, core 14 and backsheet 16 of absorbent article 110 are all identical to that of the prior embodiment and therefore share the same reference numerals. Similarly, the first layer 18 of transfer layer web 115 is identical to that of the prior embodiment and therefore shares the same reference characters. However, the second layer 119 of transfer layer web 115 differs from that of the prior embodiment.

In the embodiment shown in FIG. 2, the second layer 119 of transfer layer 115 comprises a three-dimensional apertured formed film having a male side 126 and a female side 127. A plurality of protuberances 128 having sidewalls 129 that extend from the female surface 127 in the z-direction and terminate in an aperture 130 on the male side 126. As in the prior embodiment, the protuberances 128 have a diameter equal to or less than the diameter of protuberances 22 in first layer 18.

In the embodiment of FIG. 2, the second layer 119 of transfer layer 115 further includes drains 131. The drains 131 are, like the drains 25 in the first layer 18, two-dimensional and have little or no z-direction dimension beyond the nominal thickness of the film. Drains 131 are sized to provide rapid drainage of fluids from the female side 127 to the male side 126 of second layer 119. Accordingly, they are sized with the parameters set forth above regarding drains 25. Unlike protuberances 22 and 128, there is no particular need for drains 131 to be larger or smaller than drains 25. However, if drains 131 are in fact somewhat smaller than drains 25, then there will be a measure of increased fluid distribution across surface 127 using the void volume (i.e. empty space) between protuberances 22. This is a desirable outcome causing more core exposure to the insult.

Figure 3:
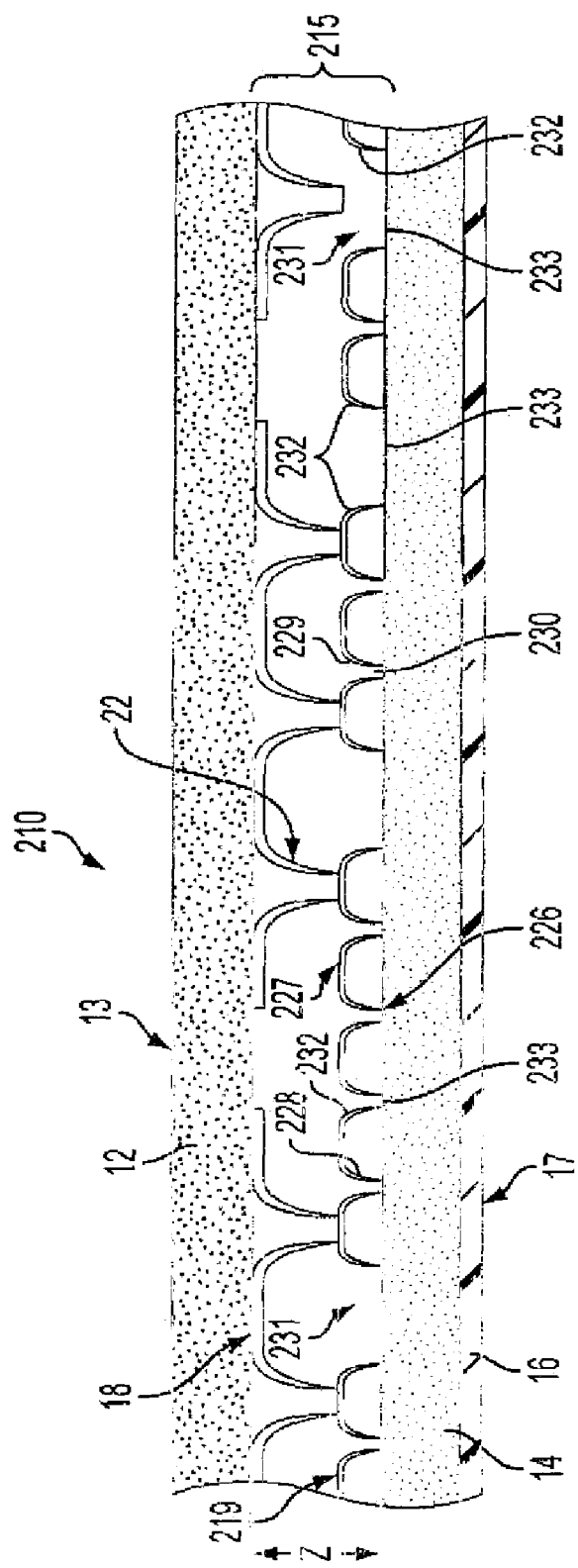
FIG. 3 is cross-sectional view of an absorbent article having a transfer layer web in accordance with yet another embodiment of the disclosure.

With reference now being made to FIG. 3, the absorbent article 210 comprises a topsheet 12, core 14 and backsheet 16 which are identical to the prior embodiments. Likewise, the first layer 18 of transfer layer 215 is identical to that of the prior embodiments. Accordingly, these features will not be further described.

In the embodiment of FIG. 3, the second layer 219 of transfer layer 215 comprises a three-dimensional apertured formed film having a male side 226 and a female side 227. A plurality of protuberances 228 having sidewalls 229 that extend from the female surface 227 in the z-direction and terminate in an aperture 230 on the male side 226. As in the prior embodiment, the protuberances 228 have a diameter equal to or less than the diameter of protuberances 22 in first layer 18.

In the embodiment of FIG. 3, the second layer 219 of transfer layer 215 further includes drains 231. Unlike the embodiment of FIG. 2, the drains 231 in this embodiment are three-dimensional and comprise sidewalls 232 that depend from the female side 227 and extend in the z-direction, terminating in an aperture 233 on the male side 226 of the film 219. The drains 231 follow the same diameter considerations as drains 25 and drains 131 in the prior embodiments to provide for rapid fluid acquisition and distribution. In order to ensure continued capillary wicking by the protuberances 228, as noted above, it is important for the apertures 230 to be in contact with a fluid removal layer, such as absorbent core 14. Accordingly, it is important for the z-direction dimension of the drains 232 to be equal to or less than the z-direction dimension of the protuberances 228.

While not shown in the Figures, it will be understood that the second layer 219 could be made to include both two-dimensional and three-dimensional drains and it need not be the case that only one or the other is used in the second layer of the transfer layers.

Figure 4:
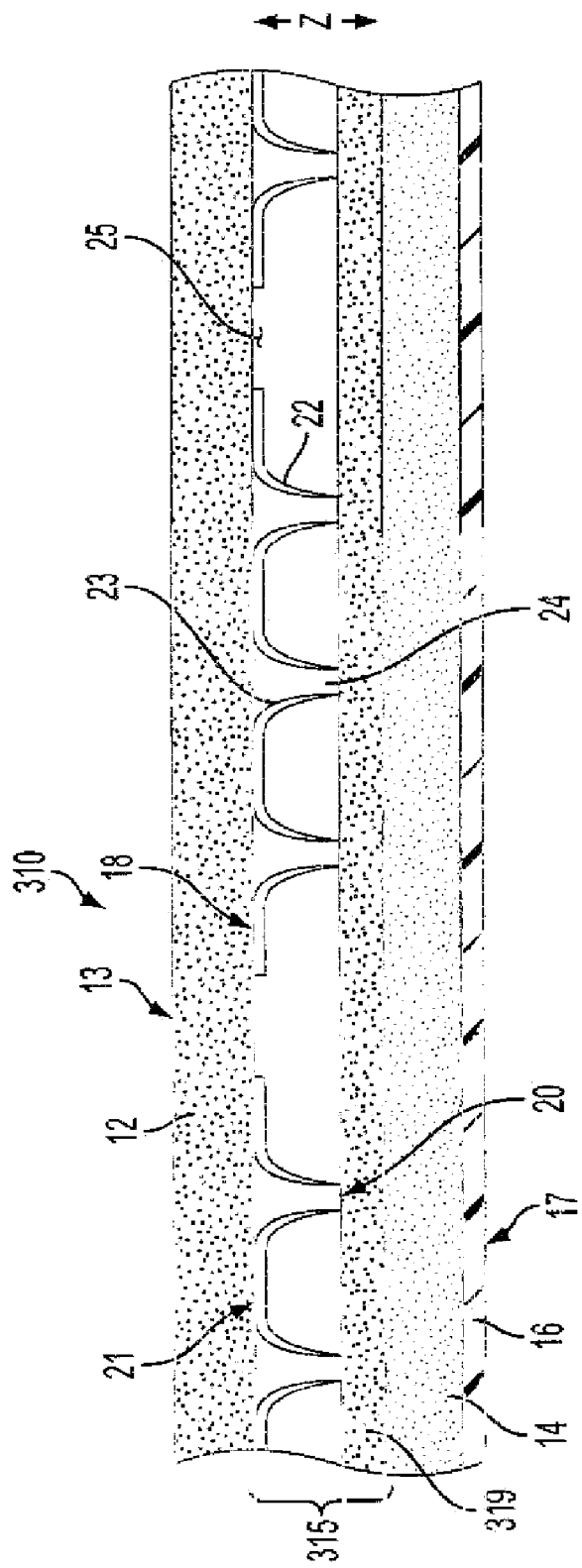
FIG. 4 is cross-sectional view of an absorbent article having a transfer layer web in accordance with yet another embodiment of the disclosure.

With reference now being made to FIG. 4, the absorbent article 310 comprises a topsheet 12, a core 14 and a backsheet 16 as in the previous embodiments, and a transfer layer 315. The transfer layer 315 in this embodiment comprises a top layer 18, which is a formed film as in the prior embodiments. The second layer 319 of transfer layer 315 in this embodiment is a nonwoven web. The nonwoven web in such embodiments should be wetted by the fluid to sustain rapid wicking to the core. Therefore it should be at least semi-phobic and it is preferable that it be hydrophilic. Basis weight is not particularly critical, other than for practical considerations. In particular, the nonwoven web should have sufficient basis weight to help lessen rewet through the drains but not so much basis weight that the transfer layer becomes too bulky, stiff, or expensive. In some embodiments, a nonwoven web having a basis weight of 8-24 grams/square meter are suitable, more specifically 8-18 grams/square meter, and most preferably 12-16 grams/square meter.

In the embodiment shown in FIGS. 1-4, the three-dimensional structures 22, 28, 128, 228, 231 are generally conical. However, is it to be understood that the shape of the three-dimensional structures in embodiments of the transfer layer is not significant. In particular, the three-dimensional structures may have a shape that is circular, oval, triangular, square, pentagonal, hexagonal, or any other desired shape. Similarly, the shape of the two-dimensional drains 25, 131 is not particularly important.

The transfer layer may be oriented in the absorbent article with either the male side or female side facing the absorbent core. In many applications, the male side of the transfer layer will face the absorbent core, but in some applications it may be desirable for the female side to face the core.

Any design or pattern may be formed to produce embodiments of the transfer layer. Any ratio of drains to capillary-sized protuberances may be used. Depending on the applications, more or fewer capillaries-sized structures may be desired as compared to the embodiments illustrated in the Figures.

It is to be understood that although this disclosure describes several embodiments, various modifications apparent to those skilled in the art may be made without departing from the invention as described in the specification and claims herein.

The invention claimed is:

1. A composite comprising;
   a first layer comprising a formed film having a plurality of capillary-sized protuberances extending in a z-direction from a female side of the first layer toward a male side of the first layer, and a plurality of two-dimensional drains formed between at least a portion of the plurality of capillary-sized protuberances at the female side of the first layer, wherein the plurality of two-dimensional drains lack a z-dimension beyond a nominal thickness of the formed film layer, and a plurality of apertures defined by ends of the plurality of protuberances at the male side of the first layer, wherein the plurality of capillary-sized protuberances comprise a diameter of between 50 microns to 400 microns at the female side of the first layer, wherein the plurality of two-dimensional drains each comprise an average diameter greater than the diameter of the plurality of capillary-sized protuberances; and a second layer in intimate contact with the ends of the capillary-sized protuberances at the male side of the first layer.

2. The composite of claim 1, wherein the second layer comprises a formed film.

3. The composite of claim 2, wherein the second layer has a plurality of capillary-sized protuberances having a smaller diameter than the diameter of the capillary-sized protuberances in the first layer and a plurality of drains.

4. The composite of claim 1, wherein the second layer comprises a nonwoven web.

5. The composite of claim 1, wherein the average diameter is between 0.55 mm and 1.2 mm.

6. The composite of claim 1, wherein the plurality of capillary-sized protuberances are cone-shaped.

7. An absorbent article comprising;

a top sheet;

a core; and a transfer layer, wherein the transfer layer comprises a first layer comprising a formed film having a plurality of capillary-sized protuberances extending in a z-direction from a female side of the first layer toward a male side of the first layer, and a plurality of two-dimensional drains formed between at least a portion of the plurality of capillary-sized protuberances at the female side of the first layer, wherein the plurality of two-dimensional drains lack a z-dimension beyond a nominal thickness of the formed film layer, and a plurality of apertures defined by ends of the plurality of protuberances at the male side of the first layer, wherein the plurality of capillary-sized protuberances comprise a diameter of between 50 microns to 400 microns at the female side of the first layer, wherein the plurality of two-dimensional drains each comprise an average diameter greater than the diameter of the plurality of capillary-sized protuberances; and a second layer in intimate contact with the ends of the capillary-sized protuberances at the male side of the first layer.

8. The article of claim 7, wherein the second layer comprises a three-dimensional apertured formed film.

9. The article of claim 8, wherein the three-dimensional apertured formed film of the second layer has a plurality of capillary-sized protuberances having a smaller diameter than the capillary-sized protuberances in the first layer and a plurality of drains.

10. The article of claim 7, wherein the average diameter is between 0.55 mm and 1.2 mm.

11. The article of claim 7, wherein the plurality of capillary-sized protuberances are cone-shaped.

12. The article of claim 7, wherein the second layer comprises a nonwoven web.

13. The article of claim 7, wherein the transfer layer is positioned between the topsheet and the core.

14. The article of claim 13, wherein the first layer of the transfer layer is closer to the topsheet than the second layer.

15. The article of claim 13, wherein the second layer of the transfer layer is closer to the topsheet than the first layer.

16. The article of claim 7, further comprising a backsheet and wherein the transfer layer is positioned between the core and the backsheet.

17. An absorbent article comprising;

a top sheet;

a transfer layer, wherein the transfer layer comprises a first layer comprising a formed film having a plurality of capillary-sized protuberances extending in a z-direction from a female side of the first layer toward a male side of the first layer, and a plurality of two-dimensional drains formed between at least a portion of the plurality of capillary-sized protuberances at the female side of the first layer, wherein the plurality of two-dimensional drains lack a z-dimension beyond a nominal thickness of the formed film layer, and a plurality of apertures defined by ends of the plurality of protuberances at the male side of the first layer, wherein the plurality of capillary-sized protuberances comprise a diameter of between 50 microns to 400 microns at the female side of the first layer, wherein the plurality of two-dimensional drains each comprise an average diameter greater than the diameter of the plurality of capillary-sized protuberances; and a second layer in intimate contact with the ends of the capillary-sized protuberances at the male side of the first layer;

an absorbent core adjacent to the second layer of the transfer layer opposite of the first layer such that the second layer is positioned between the first layer and the absorbent core; and a backsheet adjacent to the absorbent core opposite to the second layer of the transfer layer such that the absorbent core is positioned between the second layer of the transfer layer and the backsheet.

* * * * *